United States Patent [19]

Nielsen et al.

[11] Patent Number: 5,683,358
[45] Date of Patent: Nov. 4, 1997

[54] APPLICATOR FOR HOLDING AND DISPENSING A SUBSTANCE

[75] Inventors: Steven James Nielsen, Greenville; Allan James Krueger, Winneconne, both of Wis.

[73] Assignee: Kimberly-Clark Worldwide, Inc., Neenah, Wis.

[21] Appl. No.: 422,116

[22] Filed: Apr. 14, 1995

Related U.S. Application Data

[63] Continuation-in-part of Ser. No. 366,207, Dec. 29, 1994, abandoned.

[51] Int. Cl.⁶ ..................................................... A61F 13/20
[52] U.S. Cl. ..................................................... 604/11; 604/15
[58] Field of Search ..................................... 604/11, 14, 15, 604/16, 904

[56] References Cited

U.S. PATENT DOCUMENTS

| | | |
|---|---|---|
| 2,298,752 | 10/1942 | Crockford .................. 604/11 |
| 2,476,956 | 7/1969 | Bonham . |
| 2,509,241 | 5/1950 | Mende ....................... 604/11 |
| 2,739,593 | 3/1956 | McLaughlin . |
| 2,879,769 | 3/1959 | Gordon et al. . |
| 3,065,677 | 11/1962 | Loeser . |
| 3,148,680 | 9/1964 | Roberts et al. . |
| 3,347,234 | 10/1967 | Voss . |
| 3,575,169 | 4/1971 | Voss et al. . |
| 3,581,744 | 6/1971 | Voss ........................... 604/14 |
| 3,633,469 | 1/1972 | Kinney . |
| 3,760,808 | 9/1973 | Blever ........................ 604/14 |
| 4,106,396 | 8/1978 | Richards et al. . |
| 4,375,969 | 3/1983 | Woerz . |
| 4,610,659 | 9/1986 | Friese ......................... 604/11 |
| 5,330,421 | 7/1994 | Tarr et al. ................... 604/16 |
| 9,846,802 | 7/1989 | Sanders ....................... 604/15 |

FOREIGN PATENT DOCUMENTS

| | | |
|---|---|---|
| 0475690 | 3/1992 | European Pat. Off. . |
| 0605016A2 | 7/1994 | European Pat. Off. . |
| 2080061 | 11/1971 | France ........................ 604/15 |
| 1012217 | 12/1965 | United Kingdom . |

OTHER PUBLICATIONS

Article Entitled "Engineering Materials and Their Applications." Copyright 1981, 1975 by Houghton Mifflin Co.
Operating Instructions Manual of Chatillon Digital Force Instrument of Model DFI.
Operating Instructions Manual of Tension/Compression Tester Model TCM-200.

*Primary Examiner*—Mark O. Polutta
*Attorney, Agent, or Firm*—Thomas J. Connelly

[57] ABSTRACT

An applicator is disclosed which includes a thin walled member adapted to hold and dispense a substance. The thin walled member is formed from at least two separate and distinct layers and has first and second spaced apart ends. The applicator also has an outwardly extending fingergrip ring integrally formed adjacent to the second end which serves to facilitate control of the applicator, facilitate comfortable insertion of a substance into a body cavity or on an area of the skin, and easy removal of the applicator.

23 Claims, 3 Drawing Sheets

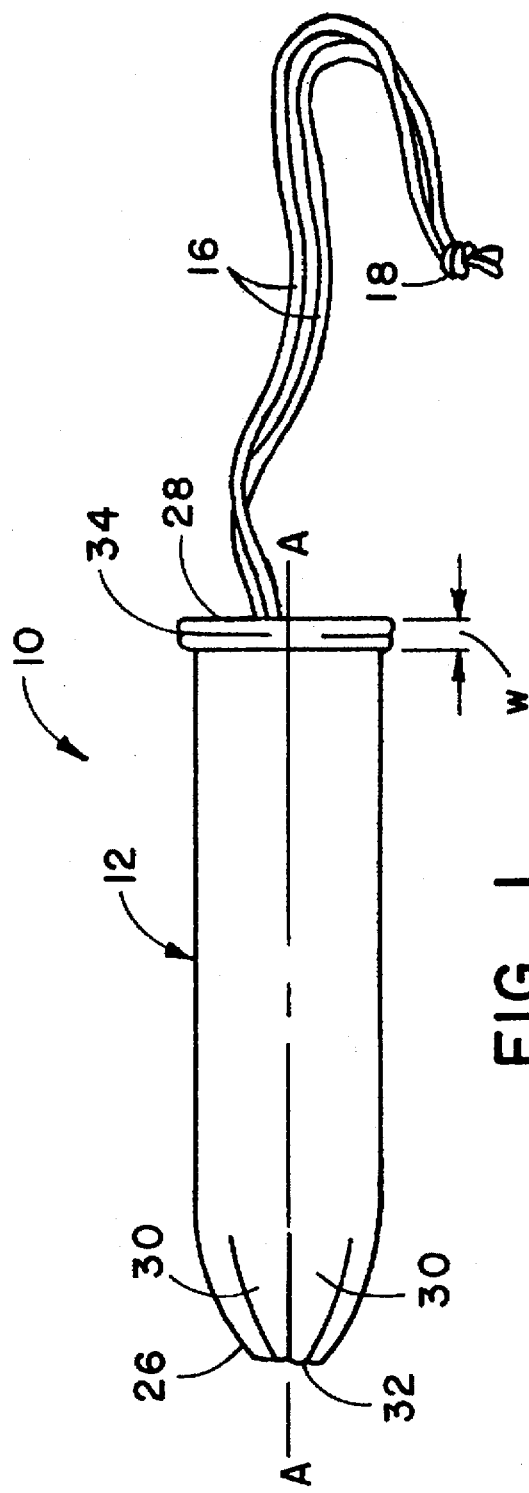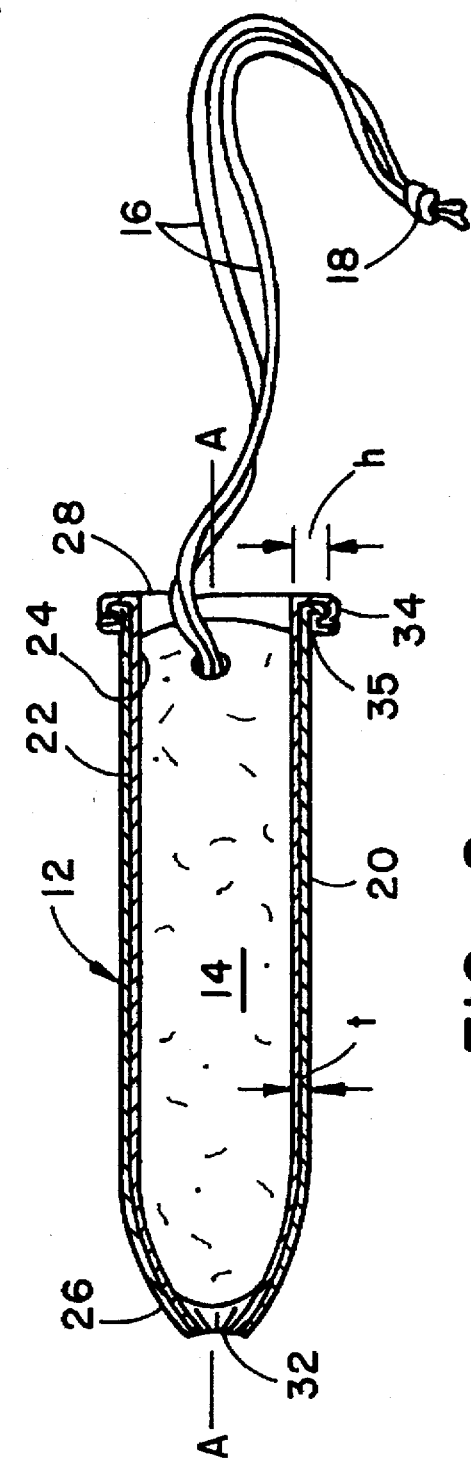

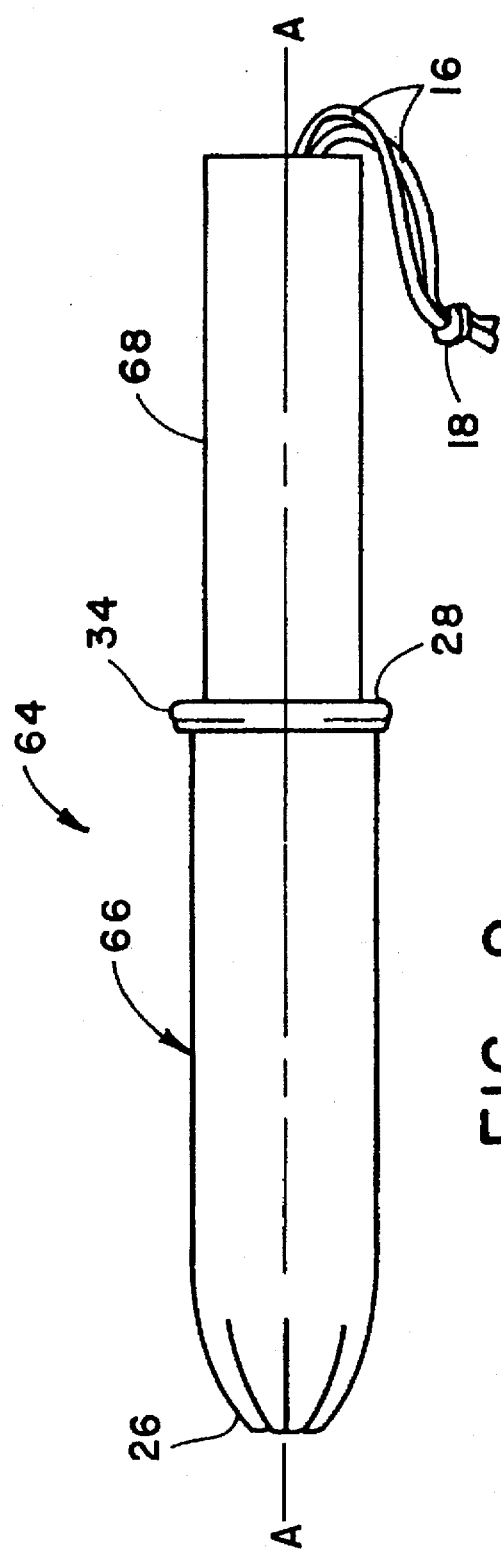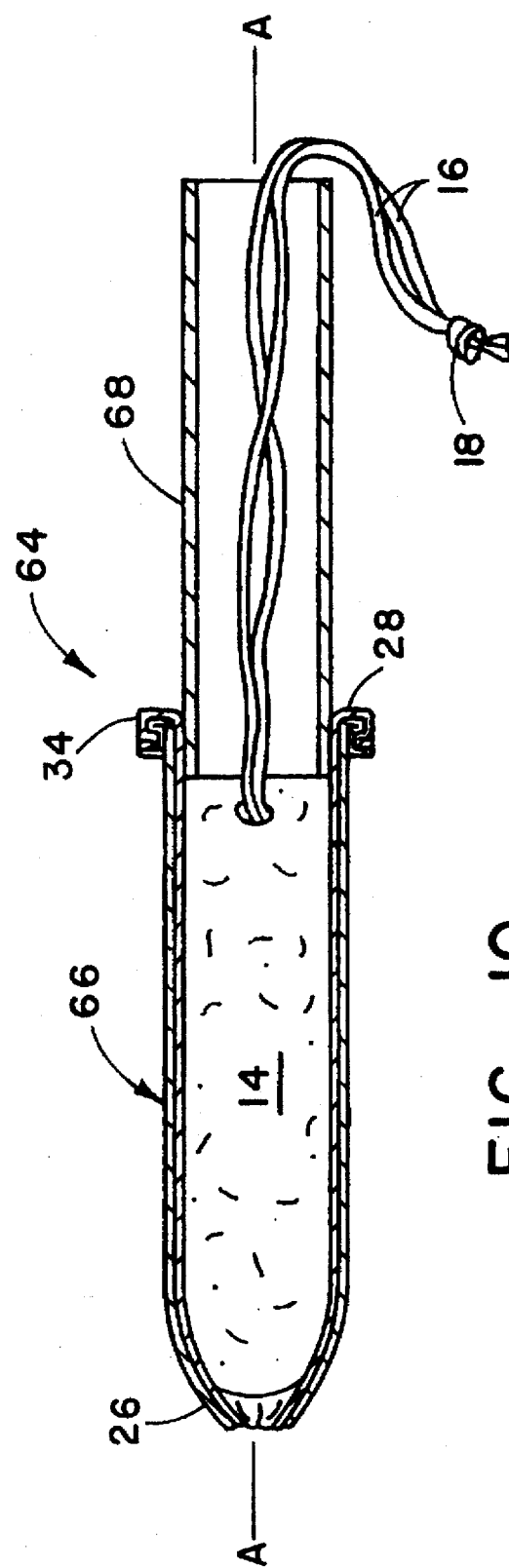

APPLICATOR FOR HOLDING AND DISPENSING A SUBSTANCE

This application is a continuation-in-part of U.S. patent application Ser. No. 08/366,207 filed Dec. 29, 1994 Abn.

FIELD OF THE INVENTION

This invention relates to an applicator adapted to hold and dispense a substance. More particularly, this invention relates to a tampon applicator having an outwardly extending, fingergrip ring integrally formed adjacent to one end thereof which serves to facilitate control of the applicator.

BACKGROUND OF THE INVENTION

Various kinds of applicators exist today which can be utilized to dispense a product or substance into a body cavity or onto the skin of a human or an animal. A tampon applicator is specifically used to insert a catamenial tampon into a woman's vagina to absorb menses, menstrual fluid, blood and other kinds of body fluid.

Tampon applicators are available in a variety of shapes and sizes. Some applicators are constructed of paper, paperboard or cardboard while others are made from plastic or are a laminate of two or more different materials. The applicator can be constructed as either a single member wherein the user utilizes her finger to expel the tampon or the applicator can be formed from two or more members. A typical two piece applicator employs two tubes which are telescopically assembled. The tubes are normally referred to as an outer tube, which houses the tampon, and an inner tube or plunger which is used to expel the tampon from the outer tube.

In using an applicator consisting of a single tubular member, the user will normally hold and position the tubular member approximate her vagina with her thumb and middle finger. She will then use her index finger to expel the tampon into her vagina. With the two piece applicator, the user will normally hold and position the outer tube of the applicator approximate her vagina with her thumb and middle finger. The inner tube is then pushed into the outer tube by movement of her index finger so as to expel the tampon into her vagina. After the tampon is expelled, the applicator is withdrawn and discarded.

It has been found that an outwardly extending fingergrip ring formed on an end of the outer tube has three primary functions. First, the fingergrip ring aids in allowing the user to control the placement of the outer tube into her vagina. Second, the fingergrip ring provides a finger stop or rest for the middle finger and thumb to counteract the forces generated while the user is expelling the tampon into her vagina. Third, the fingergrip ring facilitates removal of the outer tube from the user's vagina.

Now an applicator has been invented which contains an outwardly extending, fingergrip ring which is integrally formed on the tubular member and which facilitates proper alignment of the applicator relative to a body cavity, provide a comfortable and secure grip while inserting the dispensable substance, and ease of removal of the applicator.

SUMMARY OF THE INVENTION

Briefly, this invention relates to an applicator, especially a tampon applicator, adapted to receive and hold a dispensable product or substance. The applicator includes a thin walled member formed from at least two separate and distinct layers and having first and second spaced apart ends. The applicator also has an outwardly extending, fingergrip ring integrally formed adjacent to the second end of the thin walled member which provides a means for controlling the applicator to ensure proper alignment of the applicator relative to the body cavity. The fingergrip ring also facilitates comfortable insertion of a substance into a body cavity and ease of removal of the applicator.

The general object of this invention is to provide an applicator adapted to receive, hold and dispense a substance. A more specific object of this invention is to provide a tampon applicator having first and second spaced apart ends with an outwardly extending, fingergrip ring integrally formed adjacent to the second end which facilitates control of the applicator.

Another object of this invention is to provide a tampon applicator having an outwardly extending, fingergrip ring which facilitates removal of the applicator from a body cavity.

A further object of this invention is to provide a tampon applicator which is easy to manufacture and simple and comfortable to use.

Still another object of this invention is to provide an applicator which can be manufactured at high speeds and at a relatively low cost.

Other objects and advantages of the present invention will become more apparent to those skilled in the art in view of the following description and the accompanying drawings.

BRIEF DESCRIPTION OF THE DRAWINGS

FIG. 1 is a side view of an applicator.

FIG. 2 is a cross-sectional view of the applicator shown in FIG. 1 having a tampon pledget retained therein.

FIG. 9 is a perspective view of a two piece tampon applicator having an inner tube telescopically slidable with an outer tube.

FIG. 10 is a cross-sectional view of the two piece tampon applicator shown in FIG. 9 having a tampon pledget retained in the outer tube.

DETAILED DESCRIPTION OF THE PREFERRED EMBODIMENTS

Figure 3:
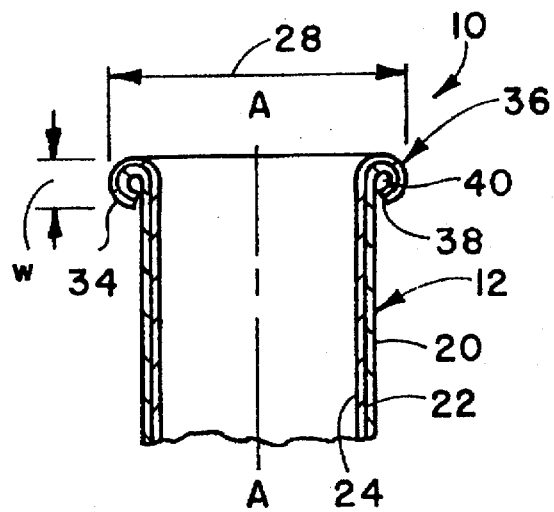
FIG. 3 is a partial cross-sectional view of the outer tube showing an integrally formed fingergrip ring having a "hollow c shaped" curl.

Referring to FIGS. 1 and 2, an applicator 10 is shown in the form of a hollow member 12 which is designed to hold a substance 14 which can be dispensed. The applicator 10 has a relatively small diameter, less than about 1 inch (about 25.4 mm). The applicator 10 also has an overall length of between about 2 to about 12 inches (about 50.8 to about 304.8 mm) although it could be shorter or longer if desired. When the applicator 10 is used as a tampon applicator, it's length should range between about 1 inch to about 3 inches (about 25.4 mm to about 76.2 mm).

The substance 14 can be almost anything, including a capsule containing medicine in a liquid, solid, granular or paste form, a medical dressing, an absorbent member, a catamenial tampon, food, etc. Although this particular invention will be described in terms of a tampon applicator 10, it should be recognized that the applicator 10 can be used to dispense a substance 14 onto the skin of a human or animal.

When the substance 14 is a tampon, it normally will include a withdrawal string 16 extending outward therefrom. The withdrawal string 16 is used to remove the soiled tampon from a woman's vagina. The withdrawal string 16 can contain a knot 18 to assure that the withdrawal string 16 does not separate from the tampon 14.

The hollow member 12 is in the shape of an elongated tube having a thin wall 20, and preferably, a circular cross-sectional profile. The wall 20 has a thickness "t" (see FIG. 2) of less than about 0.10 inches (about 2.54 mm), preferably less than about 0.03 inches (about 0.762 mm), and most preferably, less than about 0.02 inches (about 0.5 mm). The hollow member 12 is formed from at least two separate and distinct layers 22 and 24. Although only two layers 22 and 24 are depicted, the hollow member 12 could include three or more layers. The layers 22 and 24 can be formed from paper, paperboard, cardboard, plastic, thermoplastic films or any other suitable material. For purposes of this invention, a film coating on a paper layer is considered a two layer structure.

The layers 22 and 24 can be bonded together by an adhesive such as glue, by heat, by pressure, by a combination of heat and pressure, by ultrasonics or by any other known means. Alternatively, the layers 22 and 24 can be formed as a laminate sheet and later rolled into the tubular applicator 10. It is possible to form both layers 22 and 24 out of the same material if desired. However, for economical reasons, the inner layer(s) are usually formed from a less expensive material. As mentioned above, the layers 22 and 24 are formed into a hollow, tubular member 12 having an outside diameter of less than about 1 inch (about 25.4 mm). Such a relatively small diameter can be obtained by convolutely winding, spirally winding or longitudinally seaming the material together.

The material which is used to form the inner layer 24 should be capable of stretching so that the inner layer 24 can be worked into a curl. It is important that the inner most layer 24 be capable of stretching more than the adjacent outer layer(s) because it will form the exterior surface of the fingergrip ring 34. This means that the inner most layer 24 will be formed on a larger diameter than the outer layer 22 and if it is not capable of stretching more than the outer layer 22 it will tear or deform and thereby produce a poorly shaped fingergrip ring. The inner layer(s) 24 should be capable of being stretched at least 4 percent, preferably at least 6 percent, and most preferably, at least 8 percent more than the outer layer 22. The amount of stretch can be in either the machine direction or in the cross direction depending on how the hollow, tubular member 12 is formed.

It is also possible to coat or spray an additional layer onto the exterior layer 22 to give it a smooth or slick appearance and/or feel. The coating can decrease resistance between the applicator 10 and a body cavity, such as a woman's vagina, and aid in the comfortable insertion and removal of the applicator 10 into and out of the body cavity. It is also possible to color the different layers 22 and 24 so as to provide a visually distinctive appearance. For example, the outer layer 22 can be colored white while the inner layer 24 can be colored pink. When the two layers 22 and 24 are curled, the inner layer 24 will form the exterior surface of the fingergrip ring 34 such that the finished applicator 10 will be white with a pink fingergrip ring.

The applicator 10 also has first and second spaced apart ends, 26 and 28 respectively. The first end 26 can be shaped to facilitate comfortable insertion of the applicator 10 into a body cavity. The first end 26 can be rounded, have a semi-spherical shape, be tapered or bullet shaped. The first end 26 can also contain a plurality of independent petals 30 which are capable of flexing radially outward as the tampon 14 is expelled through the first end 26. Alternatively, the first end 26 can consist of a plurality of pleats (not shown) which can expand to provide a large opening so that the substance 14 can be expelled. The first end 26 could be completely closed but preferably contains a central opening 32 aligned along the central longitudinal axis A—A of the applicator 10. The opening 32 can be about 1/16 of an inch (about 1.587 mm) or larger and serves the purpose of limiting the force which must be exerted on the substance 14 to expel it from the hollow member 12. The lower the required expulsion force, the easier it is to comfortably insert the substance 14 into a body cavity. The presence of the central opening 32 also enables the user to visually inspect the applicator 10 to make sure a substance 14 is present to be dispensed.

Integrally formed on or adjacent to the second end 28 of the applicator 10 is a fingergrip ring 34. The fingergrip ring 34 extends radially outward from the central longitudinal axis A—A. The fingergrip ring 34 should have a width "w", see FIG. 1, defined as a distance measured parallel to the central longitudinal axis A—A of between about 0.02 inches to about 0.10 inches (between about 0.5 mm to about 2.54 mm) or more. Preferably, the width "w" is between about 0.05 inches to about 0.08 inches (between about 1.27 mm to about 2.03 mm). The fingergrip ring 34 also has a height "h" extending above the outer surface of the exterior layer 22 of at least about 0.1 inches (about 2.54 mm), see FIG. 2. The height of the fingergrip ring 34 can actually increase the outer diameter of the applicator 10 from between about 5 percent to about 25 percent.

It is also important that the fingergrip ring 34 have a sufficient height (h) so that it can perform it's three primary functions. In order to properly control the placement of the applicator 10 relative to the user's skin or into a body cavity, the fingergrip ring 34 should have sufficient height (h) to enable the user to feel the fingergrip ring 34 with the tips of her fingers and know where the second end 28 of the applicator 10 is located. The fingergrip ring 34 also aids in allowing the user to position the applicator 10 relative to her vagina by permitting her to pivot the applicator 10 between the tips of her thumb and middle finger. The greater the height (h) of the fingergrip ring 34, the easier it is for the user to pivot the applicator 10 in her hand. The second function is the expulsion of the tampon 14 from the hollow member 12. The fingergrip ring 34 must have a sufficient height (h) so that the user's fingertips do not slip off of the hollow member 12 when the tampon 14 is expelled out the first end 26. For good results, the outside diameter of the fingergrip ring 34 should be at least about 5 percent greater than the outside diameter of the hollow member 12. Preferably, the outside diameter of the fingergrip ring 34 should be from about 8 percent to about 20 percent greater than the outside diameter of the hollow member 12. Most preferably, the outside diameter of the fingergrip ring 34 should be from about 12 percent to about 16 percent greater than the outside diameter of the hollow member 12.

The third function of the fingergrip ring 34 is to facilitate removal of the applicator 10 away from the user's skin or away from the vagina or other body cavity. The fingergrip ring 34 should have a sufficient height (h) so that this function can be performed without having the user's fingers slip off of the applicator 10.

Referring again to FIG. 2, the fingergrip ring 34 contains a surface 35 which is essentially perpendicular to the wall 20 of the hollow member 12. This surface 35 must possess sufficient strength so that when the user's fingers exert a force on this surface 35, the first end 26 of the applicator 10 can pivot about the fingergrip ring 34. Such pivoting action facilitates positioning of the applicator 10 relative to a body cavity.

The strength and stretch characteristics of the material forming the applicator 10 will limit the maximum outside diameter of the fingergrip ring 34. The maximum outside diameter of the applicator 10 can be calculated for different kinds of material using the following formula:

$$\frac{\text{Fingergrip Ring } OD - \text{Applicator } OD}{\text{Applicator } OD} = \text{Value} \times 100 = X \text{ Percent}$$

where OD=outside diameter.

Using this formula for applicators constructed out of different kinds of paper, it has been established that the maximum diameter of the fingergrip ring 34 is about 120 percent of the outside diameter of the applicator 10. It should be noted that different materials will yield a different maximum diameter.

The fingergrip ring 34 must have a sufficient amount of strength to prevent the user's fingers from destroying or uncurling the fingergrip ring 34 during use. The fingergrip ring 34 will encounter three different periods in which a force will be directed on it. The three periods include a controlling period where the applicator is positioned relative to a body cavity, an expulsion period where the substance is expelled into the body cavity and a removal period where the applicator 10 is removed from the body cavity. The first force that the fingergrip ring 34 must be capable of withstanding is a squeezing force as the user positions the applicator 10 adjacent to and into her body cavity. Normally only two fingers are positioned on the fingergrip ring 34 and the force exerted on the fingergrip ring 34 is not uniformly distributed about the circumference thereof. Instead, the force impinges on the circumference of the fingergrip ring 34 at two arcuate locations which are spaced approximately 180 degrees apart. Each arcuate locations can encompass an area defined between about 45 degrees to about 110 degrees. The force during this period can range from about 50 grams to about 200 grams.

The second force that the fingergrip ring 34 experiences is during the expulsion period and this represents the greatest amount of force. This force will be directed onto the fingergrip ring 34 in a direction parallel to the longitudinal centerline A—A of the hollow member 12 as the substance is expelled into the body cavity. This force will be in an opposite direction to the direction in which the fingergrip ring 34 was curled. The expulsion force of many tampon applicators is in the range of about 250 grams to about 800 grams (about 0.55 lbs to about 1.75 lbs). Therefore, the strength of the fingergrip ring 34 should be at least about 250 grams (about 0.55 lbs), preferably, greater than about 800 grams (about 1.75 lbs), and most preferably, greater than about 1500 grams (about 3.30 lbs) so as to provide a degree of safety.

The third force that the fingergrip ring 34 must be capable of withstanding is the removal force when the applicator 10 is withdrawn from the body cavity. This force, like the controlling force, is in the range of about 50 grams to about 200 grams.

The strength of the fingergrip ring 34 or the amount of force it is capable of handling before deforming or uncurling, can be measured using a Chatilion force tester equipped with a digital force gauge. Both pieces of equipment are available from Chatilion having an office located at 7609 Business Park Drive, Greensboro, N.C. 27409. A tension/compression tester, model TCM-200 and a Chatilion digital force instrument, model DFI work well.

The fingergrip ring 34 provides a structure which will act as a stop for the tips of a user's thumb and finger(s) thereby allowing another finger of the user or another member to push the substance 14 out through the forward or first end 26 of the applicator 10.

The amount of curl necessary to obtain the fingergrip ring 34 can vary depending upon the configuration of the fingergrip ring 34, the kind of material used to form the applicator 10, the number of layers, the thickness of the combined layers, etc. Normally, the second end 28 of the applicator 10 will be curled upon itself for at least 180 degrees. Another way of stating this is to say that the layers 22 and 24 are curled to an extent such that at least one fold is present and the material forming the curl will be aligned parallel to the layers 22 and 24 forming the tubular member 12. In some embodiments, it may be necessary or desirable to curl the material from between about 180 degrees to about 450 degrees. A curl of between about 270 degrees to about 360 degrees is necessary for certain curl configurations.

Referring to FIGS. 3–8, several specific curl configurations are depicted. In FIG. 3 a "hollow c curl" 36 is shown formed on the second end 28 of the applicator 10. The "hollow c curl" 36 is obtained by curling both layers 22 and 24 approximately 270 degrees so that the distal end 38 of the tubular applicator 10 is brought into contact with the exterior surface of the first or outer layer 22. The "hollow c curl" 36 has a c-shaped cross-sectional configuration. In addition, the "hollow c curl" 36 contains a hollow center or void area 40.

Figure 4:
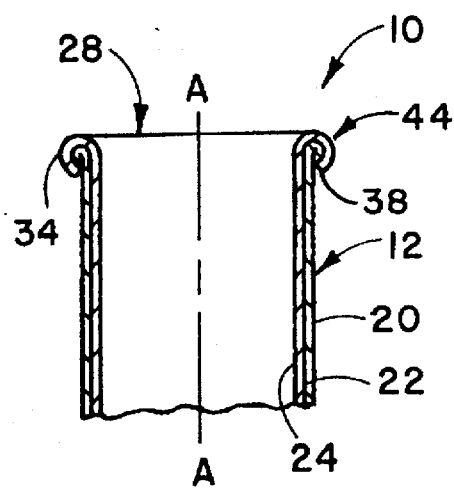
FIG. 4 is a partial cross-sectional view of the outer tube showing an integrally formed fingergrip ring having a "closed c shaped" curl.

In FIG. 4, an alternative "c curl" 44 is shown formed on the second end 28 of the applicator 10. The "c curl" 44 is obtained by curling both layers 22 and 24 approximately 270 degrees so that the distal end 38 of the tubular applicator 10 is brought into contact with the exterior surface of the first or outer layer 22. In addition, the two layers 22 and 24 are pressed during the formation process against the hollow, tubular member 12 such that no noticeable void area is present. This configuration has less open area than that shown in FIG. 3 but the curl 44 may still exhibit a limited void area.

Figure 5:
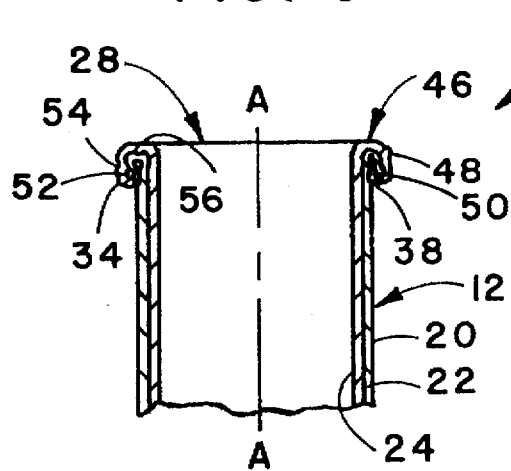
FIG. 5 is a partial cross-sectional view of the outer tube showing an integrally formed fingergrip ring having a "corrugated c shaped" curl.

Referring to FIG. 5, a "corrugated curl" 46 is shown formed on the second end 28 of the applicator 10. The "corrugated curl" 46 is obtained by curling both layers 22 and 24 approximately 270 degrees so that the distal end 38 of the tubular applicator 10 is brought into contact with the exterior surface of the first or outer layer 22. In addition, the "corrugated curl" 46 contains a hollow center or void area 48. The void area 48 gives the "corrugated curl" 46 a lesser density than the material forming the tubular wall 20. As the "corrugated curl" 46 is being formed, the material of both layers 22 and 24 is shaped into folds having alternating ridges 50 and grooves 52. The ridges 50 and grooves 52 can occur on both the outside and inside surfaces, 54 and 56 respectively, of the "corrugated curl" 46. The ridges 50 and the grooves 52 on the outside surface 54 will provide a roughened surface which is less likely to slip in a user's hand.

Figure 6:
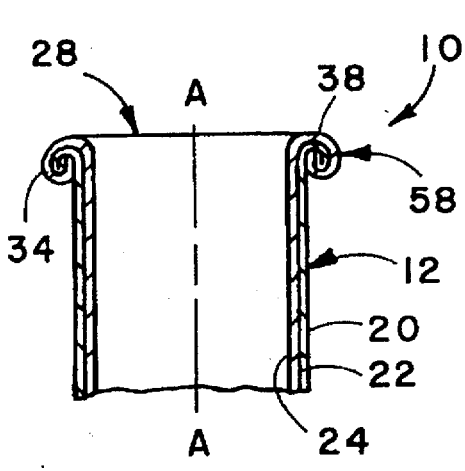
FIG. 6 is a partial cross-sectional view of the outer tube showing an integrally formed fingergrip ring having an "e shaped" curl.

Referring to FIG. 6, an "e curl" 58 is shown formed on the second end 28 of the applicator 10. The "e curl" 58 has the appearance of a backward "e" cross-sectional configuration oriented parallel to the longitudinal axis A—A. The "e curl" is obtained by curling both layers 22 and 24 approximately 360 degrees so that the distal end 38 of the tubular applicator 10 is brought into parallel alignment with the outer layer 22 and is located adjacent thereto. In this particular embodiment, a void area is not present. However, depending upon the amount of compression, if any, that is applied during and/or after curling, a void area may be present along the fold lines of the "e curl." It should also be recognized that by stretching and curling the first and second layers, 22 and 24 respectively, the fingergrip ring 34 may be formed with a lesser density than the material forming the tubular wall 20.

Figure 7:
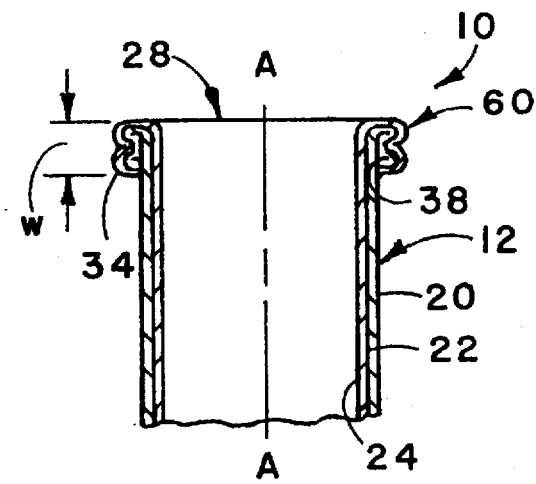
FIG. 7 is a partial cross-sectional view of the outer tube showing an integrally formed fingergrip ring having a "right s shaped" curl.
Figure 8:
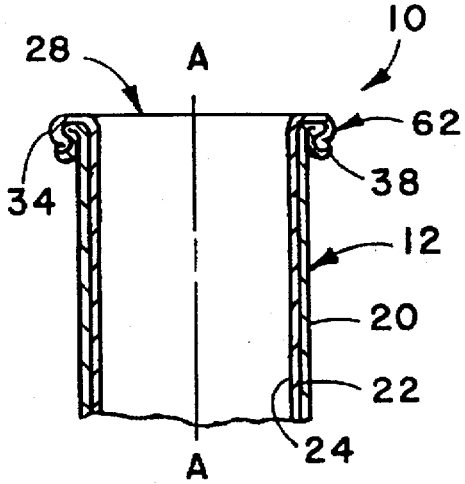
FIG. 8 is a partial cross-sectional view of the outer tube showing an integrally formed fingergrip ring having a "left s shaped" curl.

Referring to FIGS. 7 and 8, two different versions of an s-shaped curl are shown formed on the second end 28 of the applicator 10. In FIG. 7, a "right s curl" 60 is depicted while in FIG. 8, a "left s curl" 62 is shown. In the "right s curl" 60, an s-shape is obtained with the free end of the "s" being positioned adjacent to and in contact with the exterior surface of the first or outer layer 22. In the "left s curl" 62, an s-shape is obtained with the free end of the "s" being positioned away from and aligned approximately 90 degrees relative to the exterior surface of the first or outer layer 22. The right and left "s curls," 60 and 62 respectively, have an s-shaped cross-sectional configuration.

It should be noted that even though several specific curl configurations are described and shown, other curl designs are possible and may be employed without departing from the present invention. Referring again to FIGS. 3–8, the amount of material which is present in the fingergrip ring 34 is best described when looking at a cross-sectional view of the curl. When viewing the cross-sectional views, one will notice that each curl is comprised of tube wall material and usually some amount of void area 40. Given that the tube wall is made from less expensive material and is typically multilayered, it has a thickness that is somewhat substantial. This gives the applicator sufficient strength to withstand the external pressures exerted on it. The outward extending fingergrip ring 34 must also have sufficient strength and height to function properly in use. The outside diameter of the fingergrip ring 34 is substantially greater than the outside diameter of the tube and this means that the paper fibers are altered or stretched in order to occupy the larger diameter of the fingergrip ring 34. Consequently, the type of material, the thickness of the material, the amount of stretch of the material, the initial outside diameter of the tube, and the outside diameter of the fingergrip ring 34 are all interrelated. Accordingly, two terms that will be used to describe this interaction are "cross-sectional area" and "wall density" of the fingergrip ring 34.

The "cross-sectional area" of each fingergrip ring 34 is comprised of a percentage of tube material and a complementary percentage of void area 40. The cross-sectional area of each fingergrip ring 34 is comprised of from between about 70 percent to about 95 percent of material and a complementary void area of between about 5 percent to about 30 percent. Preferably, the cross-sectional area of each fingergrip ring 34 is comprised of from between about 80 percent to about 90 percent of material and a complementary void area of between about 10 percent to about 20 percent.

This is a much greater percent of material in the fingergrip ring 34 than what is present in existing paper drinking cups where the amount of material present in the curl is between about 10 percent to about 20 percent and the void area is between about 80 percent to about 90 percent. The ratio of material to void area in a fingergrip ring 34 is determined by the type of material from which the ring is formed, the particular height dimension "h" needed, the required strength needed, etc. It has been found that the height and strength of the fingergrip ring 34 are crucial parameters in determining how effective the fingergrip ring 34 is in aiding control, insertion and removal to the applicator 10.

The "wall density" of each fingergrip ring 34 is determined using the standard definition of density as defined by "Engineering Materials & Their Application," 2nd edition, page 52, published by Flinn/Trojan, copyrighted 1981. Density is defined as "mass divided by volume" and is usually expressed in terms of grams per cubic centimeter or kilograms per cubic meter. In order to form a suitable fingergrip ring 34, the tubular wall 20 should have a density of between about 0.4 grams per cubic centimeters to about 1.0 grams per cubic centimeters. For a two ply paper applicator, a density of about 0.6 grams per cubic centimeters works well. The density of the wall which forms the fingergrip ring 34 is preferably less than the density of the tubular wall 20. However, an acceptable range is between about 20 percent less than the density of the tubular wall 20 to about 20 percent greater than the density of the tubular wall 20.

The fingergrip ring 34 can be formed by contacting one end of the circumference of the hollow member 12 with a rotating tool. The tool contacts the hollow member 12 and moves parallel to its longitudinal centerline A—A. An apparatus for forming a curl on an end of a tubular member is taught in co-pending U.S. Ser. No. 08/366,074 filed Dec. 29, 1994 now U.S. Pat. No. 5,614,230 and is incorporated hereby reference and made a part hereof. As the tubular wall 20 is curled into a fingergrip ring 34, the fibers of the inner layer 24, assuming the inner layer 24 is constructed of a material like paper, are stretched and worked. This causes the fibers to be separated or become spaced out on a microscopic scale. The density of the material consequently decreases. If the fingergrip ring 34 is not subsequently compressed, it will be less dense than the hollow member 12 and may contain a void area. It is possible to compress the fingergrip ring 34 and reduce or eliminate the void area. This will cause the fingergrip ring 34 to become more dense. The fingergrip ring 34 could be compressed such that it has a higher density than the tubular wall 20 from which it was formed. However, too much compression creates an unacceptable weak fingergrip ring 34. If the density at the top of the fingergrip ring 34 is increased too much, the fingergrip ring 34 can become brittle and a weak hinge point is thereby created. This is undesirable when using of the fingergrip ring 34 on a tampon applicator 10.

Referring now to FIGS. 9 and 10, a two piece tampon applicator 64 is depicted which includes a first member 66 and a second member 68. The first member 66, or outer tube as it is sometimes referred to, is hollow and is sized and configured to receive and retain a catamenial tampon 14. The first member 66 has an outside diameter of less than about 1 inch (about 25.4 mm), preferably less than about 0.75 inches (about 19.05 mm), and most preferably, less than about 0.625 inches (about 15.875 mm). The first member 66 can be constructed as taught above for the hollow member 12 and should contain at least two separate and distinct layers. Preferably, at least one of the layers is paper. The second member 68, or inner tube as it is sometimes referred to, is sized and configured to telescopically slide within the inner circumference of the first member 66. The second member 68 is preferably hollow although it does not have to be. As the second member 68 is pushed into the first member 66, the tampon 14 is expelled through the forward end 26 of the first member 66. After the tampon 14 is positioned in a woman's vagina, the applicator 64 is properly discarded.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An applicator comprising a thin walled member adapted to hold and dispense a substance, said member being formed from at least two separate and distinct layers, said layers including an inner layer and an outer layer with said inner layer being more stretchable than said outer layer, said member having first and second spaced apart ends and an outwardly extending fingergrip ring integrally formed adjacent to said second end from said inner and outer layers.

2. The applicator of claim 1 wherein said fingergrip ring has a density less than that of said walled member.

3. The applicator of claim 2 wherein said fingergrip ring has a density which is up to about 20 percent less than the density of said walled member.

4. The applicator of claim 1 wherein said fingergrip ring is comprised of between about 70 percent to about 95 percent material and between about 5 percent to about 30 percent void area.

5. The applicator of claim 1 wherein said fingergrip ring is comprised of between about 80 percent to about 90 percent material and between about 10 percent to about 20 percent void area.

6. An applicator comprising a hollow, thin walled member adapted to hold and dispense a substance, said member being formed from at least two separate and distinct layers, said layers including an inner layer and an outer layer with said inner layer being more stretchable than said outer layer, said member having first and second spaced apart ends and an outwardly extending fingergrip ring integrally formed adjacent to said second end from said inner and outer layers, said fingergrip ring being formed by curling said second end of said applicator upon itself for at least 180 degrees.

7. The applicator of claim 6 wherein said fingergrip ring is formed by curling said second end of said applicator upon itself for at least 270 degrees.

8. The applicator of claim 6 wherein said fingergrip ring is formed by curling said second end of said applicator upon itself for about 360 degrees.

9. An applicator comprising a hollow, thin walled member adapted to hold and dispense a substance, said member being formed from at least two separate and distinct layers, said layers including an inner layer and an outer layer with said inner layer being more stretchable than said outer layer, said member having a central longitudinal axis, first and second spaced apart ends and an outwardly extending fingergrip ring integrally formed adjacent to said second end from said inner and outer layers, said fingergrip ring being formed by curling said second end of said applicator upon itself for at least 180 degrees, and said fingergrip ring being capable of withstanding a force of at least 250 grams applied thereon at a direction parallel to said central longitudinal axis.

10. The applicator of claim 9 wherein said thin walled member contains an inner layer and an outer layer and said inner layer is capable of stretching at least about 4 percent more than said outer layer.

11. The applicator of claim 10 wherein said inner layer is bonded to said outer layer by an adhesive.

12. The applicator of claim 9 wherein said fingergrip ring is comprised of between about 70 percent to about 95 percent material and between about 5 percent to about 30 percent void area.

13. The applicator of claim 9 wherein said fingergrip ring is comprised of between about 80 percent to about 90 percent material and between about 10 percent to about 20 percent void area.

14. The applicator of claim 9 wherein said ring has a c-shaped cross-sectional configuration.

15. The applicator of claim 9 wherein said ring has an e-shaped cross-sectional configuration.

16. The applicator of claim 9 wherein said ring has an s-shaped cross-sectional configuration.

17. The applicator of claim 9 wherein said inner layer is capable of stretching at least 6 percent more than said outer layer.

18. The applicator of claim 9 wherein said inner layer is capable of stretching at least 8 percent more than said outer layer.

19. A tampon applicator comprising:

a) a first member adapted to hold and dispense a tampon, said first member being formed from at least two separate and distinct layers, said layers including an inner layer and an outer layer with said inner layer being more stretchable than said outer layer, said member having first and second spaced apart ends and an outwardly extending ring integrally formed adjacent to said second end from said inner and outer layers; and b) a second member telescopically slidable within said first member, said second member adapted to expel said tampon as it is moved into said first member.

20. The applicator of claim 18 wherein said first member has an outside diameter of less than about 1 inch.

21. The applicator of claim 20 wherein said first member has an outside diameter of less than about 0.75 inches.

22. The applicator of claim 19 wherein said first member is formed from at least three separate and distinct layers.

23. The applicator of claim 19 wherein one of said layer is paper.

* * * * *